US00PP26596P3

(12) United States Plant Patent
Olesen

(10) Patent No.: US PP26,596 P3
(45) Date of Patent: Apr. 12, 2016

(54) MINIATURE ROSE PLANT NAMED 'POULTY016'

(50) Latin Name: ***Rosa* hybrid**
Varietal Denomination: Poulty016

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 239 days.

(21) Appl. No.: 13/986,930

(22) Filed: Jun. 14, 2013

(65) Prior Publication Data

US 2014/0373214 P1 Dec. 18, 2014

(51) Int. Cl.
*A01H 5/00* (2006.01)
*A01H 5/02* (2006.01)

(52) U.S. Cl.
USPC ..... Plt./120
CPC ..... *A01H 5/0222* (2013.01)

(58) Field of Classification Search
USPC ..... Plt./120
See application file for complete search history.

(56) References Cited

PUBLICATIONS

Perfection by Poulsen Indoor roses Main Varieties 2013. Jan. 2013.*

* cited by examiner

*Primary Examiner* — Annette Para

(57) ABSTRACT

A new miniature rose plant that has abundant, orange pink blend flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulty016'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2007 and the resulting seeds were planted in a controlled environment in Fredensborg, Denmark. The new variety, named 'Poulty016', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant orange pink blend flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulty016' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulty016' was selected by the inventor as a single plant from the progeny of the hybridization in 2007.

Asexual reproduction of 'Poulty016' by cuttings was first done by Mogens N. Olesen in the nursery in Fredensborg, Denmark 2008. This initial and other subsequent propagations conducted in controlled environments have demonstrated that the characteristics of 'Poulty016' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulty016'. Specifically illustrated in the drawing are flowers at various stages of development, flower in parts, leaves, and stems.

DETAILED DESCRIPTION OF THE VARIETY

The following is a description of 'Poulty016', as observed in its growth in glasshouses in Burlington, Ontario, Canada. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulcar', U.S. Plant Pat. No. 7,999 are compared to 'Poulty016' in Chart 1.

CHART 1

| | 'Poulty016' | 'Poulcar' |
|---|---|---|
| Petalage: | 45 petals total, 7 of which are petaloids | 60 |
| Flower Diameter: | 35 mm | 1.25 inch (31 mm) |
| Upper petal color: | Red Group 38A at marginal zone with Orange-Red Group 33D at middle zone, Yellow-Orange Group 18C at basal zone | Red Group 38C |

FLOWER AND FLOWER BUD

Blooming habit: Continuous.

Flower bud:

*Size*.—Upon opening, 20 mm in length from base of receptacle to end of bud. 11 mm in diameter.

*Bud form*.—Ovate.

*Bud color*.—As sepals unfold, petals are Red Group 41D.

*Sepals*.—Upper Surface: Color: Green Group 138A. Texture: Smooth and pubescent. Lower Surface: Color: Yellow Green Group 146B. Texture: Smooth with stipitate glands. Shape: Apex: Cirrhose. Base: Flat at union with receptacle. Margins: Margins have moderate foliaceous appendages on three of the five sepals. Size: 22 mm long by 6 mm wide.

*Receptacle*.—Surface Texture: Smooth. Shape: Campanulate. Size: 10 mm tall and 10 mm wide. Color: Yellow Green Group 144A.

*Pedicel*.—Surface: Smooth. Many stipitate glands. Length: 20 to 25 mm. Diameter: Generally 2.5 mm. Color: Yellow-Green Group 144A. Strength: Medium strength.

*Borne*.—Singly.

Flower bloom:

*Fragrance*.—Light floral scent.

*Duration*.—As a pot plant, flowers last up to 28 days.

*Size*.—Flower diameter is 35 mm when open. Flower depth is 15 mm.

*Form*.—General shape is a rosette.

*Shape of flower, side view*.—Upon opening, the upper portion is flattened convex. The lower portion is a flattened convex.

Petalage: Under normal conditions, flowers have 45 petals total, 7 of which are petaloids.

Color:

*General tonality*.—On open flower Red Group 41D.

*Upon opening, petals*.—The upper surfaces of outer and inner petals are Orange Group 29B with margins the color of Red Group 41D. Orange 29B splashed with Orange Group 25D on the lower surface. At the base of the petal, the upper surface is Yellow Orange Group 14D. No basal petal spot on the lower surface.

*After opening, petals*.—The upper surfaces of outer and inner petals are Red Group 38A at marginal zone with Orange-Red Group 33D at middle zone, Yellow-Orange Group 18C at basal zone. The lower surface is Orange 29B splashed with Orange Group 25D.

Petals:

*Petal reflex*.—Moderate.

*Margin*.—Entire.

*Shape*.—Generally narrow elliptic. Apex shape: Rounded. Base shape: Acute.

*Size*.—18 mm (l) by 18 mm (w).

*Texture*.—Smooth.

*Thickness*.—Average.

Petaloids:

*Quantity*.—7 on average.

*Size*.—10 mm (l) by 6 mm (w).

*Shape*.—Irregular, and asymmetric. The apex and base are acute. Color: The upper surface is Orange Group 29B with marginal intonations of Red Group 41D. Orange 29B splashed with Orange Group 25D on the lower surface. At the base of the petaloids the upper surface is Yellow Orange Group 14D. No basal petaloid spots observed on the lower surface.

Reproductive organs:

*Pollen*.—None Observed.

*Anthers*.—Size: 1.5 mm long. Color: Green-Yellow Group 1B. Quantity: 25 on average.

*Filaments*.—Color: Yellow Group 4D. Length: About 5 mm.

*Pistils*.—Length: About 4 mm long. Quantity: 20 on average.

*Stigmas*.—Slightly inferior relative to the length of the filaments and the height of the anthers. Color: Green White Group 157B.

*Styles*.—Color: Green White Group 157B.

*Seed formation*.—Not observed.

PLANT

Plant growth: Upright. Plants are 15 cm in height, and 15 cm wide.

Stems:

*Color*.—Juvenile growth: Yellow-Green Group 144C. Mature growth: Yellow-Green Group 146A.

*Length*.—Canes are 11 cm from the base of the plant to the flowering portion.

*Diameter*.—3 to 4 mm.

*Internodes*.—On mature canes, there is an average distance of 25 mm between nodes.

*Surface texture*.—Young and mature wood is smooth.

Prickles:

*Incidence*.—3 per 10 cm of stem.

*Size*.—Average length: 3 mm.

*Color*.—Juvenile prickles are Greyed Red Group 178B. Mature prickles are Greyed Red Group 178B.

*Shape*.—Linear.

Plant foliage:

*Compound leaf size*.—65 mm (l) by 45 mm (w).

*Quantity*.—3 leaves per 10 cm of stem.

*Color of juvenile foliage*.—Upper Leaf Surface: Yellow-Green Group 146B with intonations of Greyed-Orange Group 175A. Lower Leaf Surface: Greyed-Orange Group 176B with intonations of Yellow-Green Group 146B.

*Color of mature foliage*.—Upper Leaf Surface: Yellow-Green Group 147A. Lower Leaf Surface: Yellow-Green Group 147B.

Plant leaves and leaflets:

*Stipules*.—Size: About 3 mm in length. Shape: Linear, slightly broad based with outward extending apecies. Margins: Finely serrated with few stipitate glands. Color: Yellow-Green Group 146B.

*Petiole*.—Length: 13 mm on average. Diameter: About 1 mm. Upper surface: Yellow-Green Group 146A. Lower surface: Yellow-Green Group 144B.

*Rachis*.—Length: 25 mm on average. Diameter: About 2 mm. Upper surface: Yellow-Green Group 146A. Many stipitate glands. Lower surface: Yellow-Green Group 144B. Small prickles.

Leaflet:

*Number of leaflets*.—5 on normal leaves in middle of the stem.

*Size*.—26 mm in length by 18 mm wide.

*Margin*.—Serrate.

*General shape*.—Elliptical.

*Apex shape*.—Acute.

*Base shape*.—Round.

*Texture*.—Smooth.

*Arrangement*.—Odd pinnate.

*Venation*.—Reticulate.

*Leaf gloss*.—Glossy.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulty016', substantially as illustrated and described herein, due to its abundant, orange pink blend flowers, vigorous growth, compact habit, suitability for production from softwood cuttings in pots, and durable flowers and foliage that make the variety suitable for distribution in the floral industry.

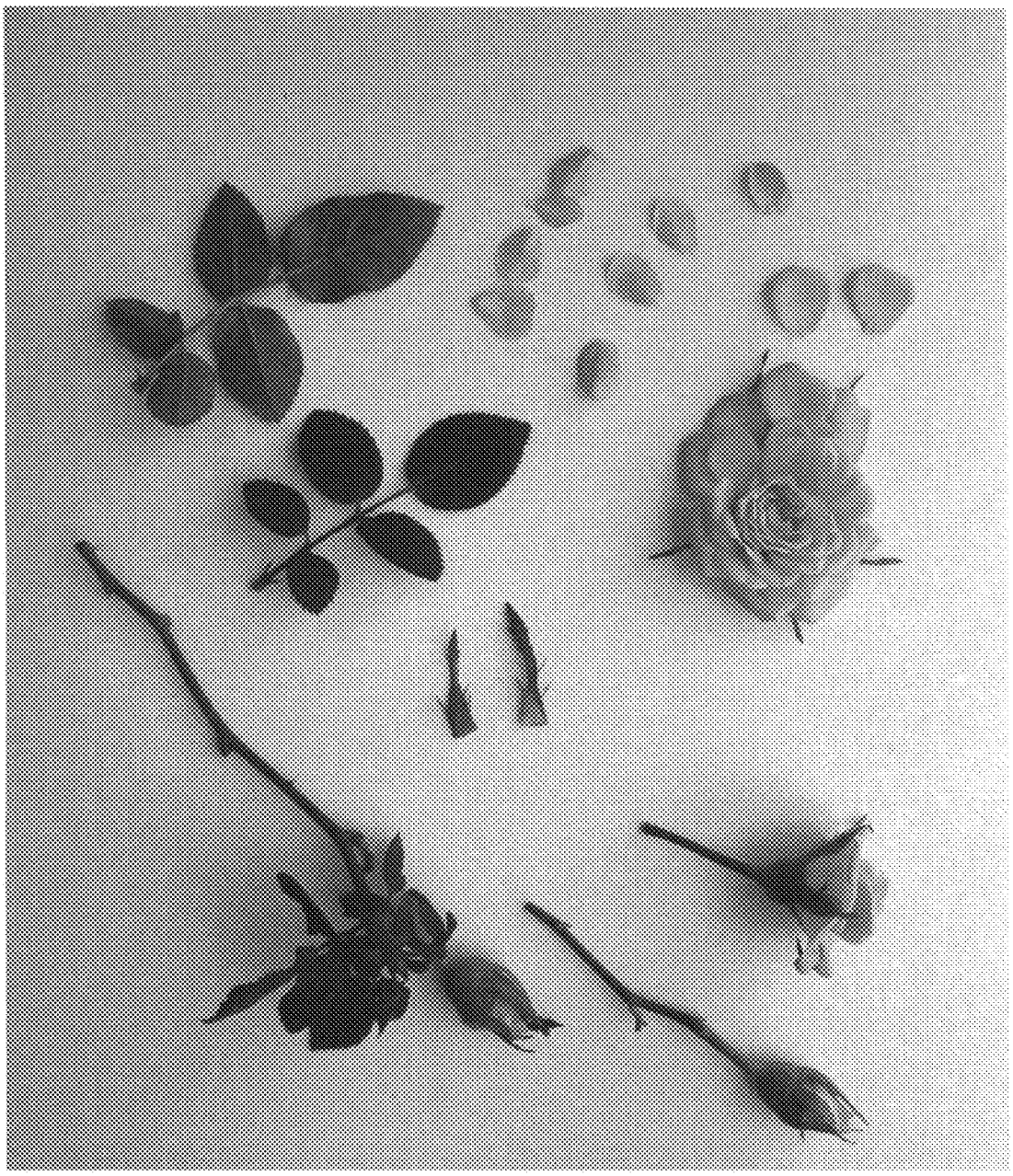

* * * * *